United States Patent
Ray et al.

(10) Patent No.: US 12,347,009 B2
(45) Date of Patent: Jul. 1, 2025

(54) MODIFYING AVATARS IN USER INTERFACES BASED ON WEARABLE DEVICE DATA USING MACHINE LEARNING

(71) Applicant: Red Hat, Inc., Raleigh, NC (US)

(72) Inventors: Debarshi Ray, Brno (CZ); Carlos Soriano Sanchez, Brno (CZ)

(73) Assignee: Red Hat, Inc., Raleigh, NC (US)

( * ) Notice: Subject to any disclaimer, the term of this patent is extended or adjusted under 35 U.S.C. 154(b) by 218 days.

(21) Appl. No.: 17/984,389

(22) Filed: Nov. 10, 2022

(65) Prior Publication Data

US 2024/0161373 A1 May 16, 2024

(51) Int. Cl.
*G06T 13/40* (2011.01)
*A61B 5/16* (2006.01)
*G06N 3/08* (2023.01)

(52) U.S. Cl.
CPC .............. *G06T 13/40* (2013.01); *A61B 5/165* (2013.01); *G06N 3/08* (2013.01)

(58) Field of Classification Search
None
See application file for complete search history.

(56) References Cited

U.S. PATENT DOCUMENTS

| | | | |
|---|---|---|---|
| 2018/0181854 A1 | 6/2018 | Koukoumidis et al. | |
| 2019/0172242 A1* | 6/2019 | Bullivant | G06N 3/004 |
| 2020/0372221 A1 | 11/2020 | Phillips et al. | |
| 2021/0350917 A1 | 11/2021 | Curtis | |
| 2023/0154093 A1* | 5/2023 | Bae | G06V 40/174 |
| | | | 345/633 |
| 2024/0153182 A1* | 5/2024 | Volk | G06F 3/011 |

* cited by examiner

*Primary Examiner* — Nurun Flora
(74) *Attorney, Agent, or Firm* — Kilpatrick Townsend & Stockton LLP

(57) ABSTRACT

Some examples described herein relate to modifying avatars in user interfaces based on wearable device data using machine learning. For example, a system can receive, from a wearable device, a set of biological data with respect to a user wearing the wearable device. The user can be associated with an avatar of the user on a user interface. The system can provide the avatar of the user and the set of biological data as input to a trained machine-learning model. The trained machine-learning model can generate a modified avatar based on the input. The system can then receive the modified avatar as output from the trained machine-learning model. The system can modify the user interface to include the modified avatar. The modified avatar can be outputted for display on a client device.

14 Claims, 5 Drawing Sheets

MODIFYING AVATARS IN USER INTERFACES BASED ON WEARABLE DEVICE DATA USING MACHINE LEARNING

TECHNICAL FIELD

The present disclosure relates generally to machine learning and, more particularly (although not necessarily exclusively), to using machine learning to modify avatars in user interfaces based on wearable computer data.

BACKGROUND

Machine-learning models have recently grown in popularity. A machine-learning model can be an algorithm that is trained using training data to make predictions or decisions. The machine-learning model may detect patterns within training data and these patterns may be used to make predictions or decisions in relation to new data.

DETAILED DESCRIPTION

Figure 1:
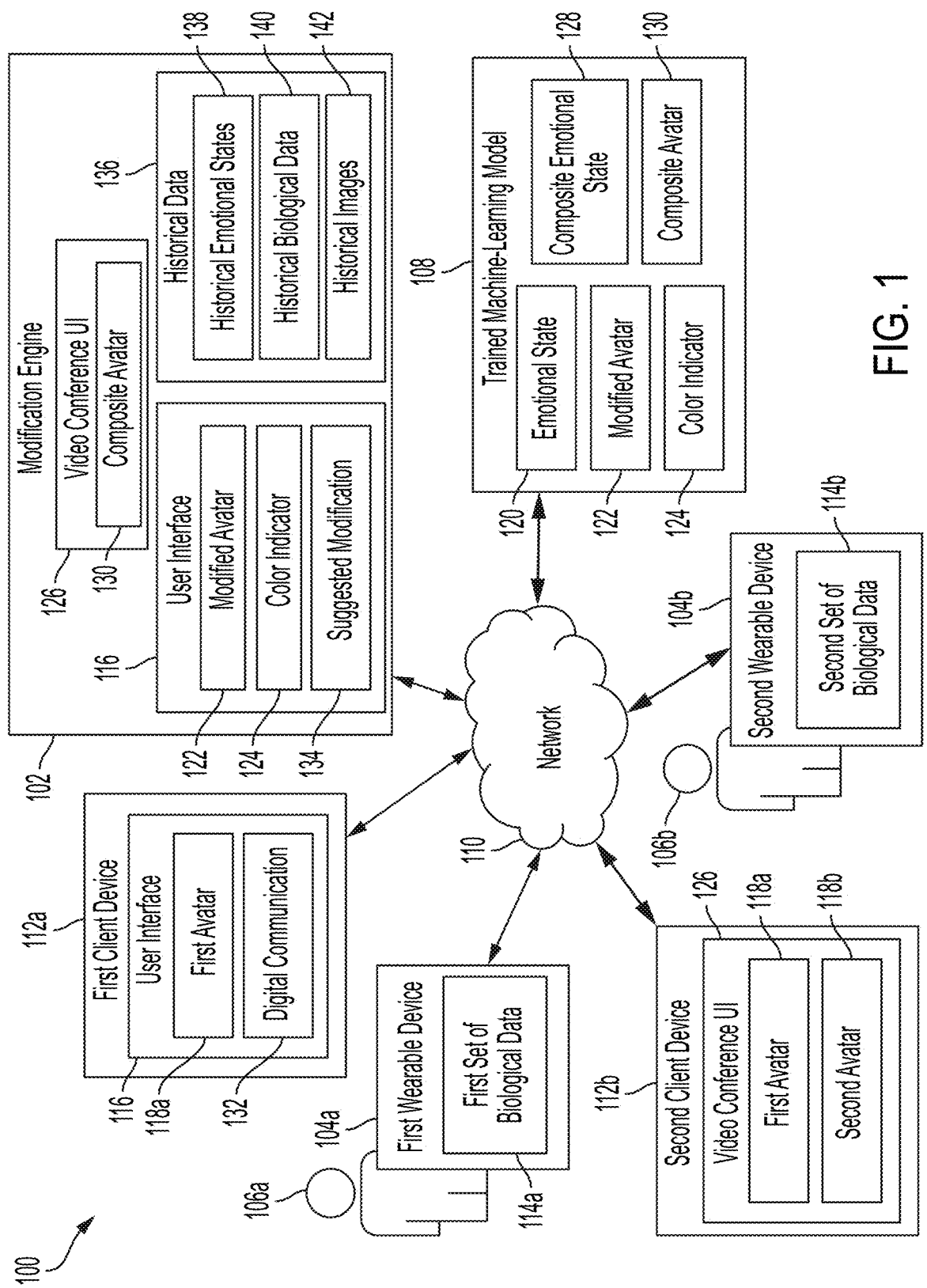
FIG. 1 is a block diagram of an example of a computing environment for using machine learning to modify an avatar on a user interface according to some examples of the present disclosure.

Electronic communication, especially when based on text, can lack non-verbal cues that are otherwise present in other forms of human interaction. In some examples, humans may have a tendency to be more aggressive on electronic communication than they may be if they were to instead interact face to face. Additionally, the lack of non-verbal cues can cause a recipient of the electronic communication to misinterpret the electronic communication as being more aggressive than was intended by the sender. In some instances, participants in video conferencing calls may turn off their video. It may be difficult for a speaker in the video conferencing call to gauge audience reactions to the speaker's presentation.

Some examples of the present disclosure overcome one or more of the abovementioned problems by using machine learning to modify avatars in user interfaces based on biological data received from wearable devices. Avatars often depict a cartoon illustration or camera picture of users on user interfaces. Such avatars are typically static images that do not change. By inputting an avatar and biological data collected from a wearable device for the user into a trained machine-learning model, a modified avatar can be generated as output. The modified avatar can display an emotional state of the user detected from the biological data. For example, the modified avatar may display facial expressions such as smiling, laughing, frowning, yawning, crying, grimacing, or more based on the biological data. The modified avatar can be included in messages sent via the user interface. Thus, recipients of the messages can have further context for a particular message based on the emotional state displayed by the modified avatar, and may be less likely to misinterpret the message. Such modified avatars can also be displayed on video conference calls. In some examples, machine learning can additionally be used to generate a composite avatar of all users on the video conference call. Displaying the composite avatar that reflects a composite emotional state of the users can communicate the emotional states of users who are not participating via video.

In one particular example, a user can interact with a user interface on a client device to compose and send an email. The user interface can include an avatar, such as a picture of the user, within each email. The user may wear a wearable device such as an activity tracker worn on their wrist. A computing system can detect that an email is being composed via the user interface, and in response can request that the wearable device transmit biological data collected on the user. The wearable device can transmit biological data collected within a certain predetermined time frame, such as within the last day or week. The computing system can input the avatar for the user and the biological data as input to a trained machine-learning model. The trained machine-learning model can output a modified avatar that reflects an emotional state of the user based on the biological data. When the user sends the email via the user interface, the computing system can modify the user interface to replace the avatar with the modified avatar. Thus, when a recipient receives the email, the modified avatar in the user interface can indicate the emotional state of the user when the email was sent.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a block diagram of an example of a computing environment 100 for using machine learning to modify an avatar on a user interface 116 according to some examples of the present disclosure. The computing environment 100 can include a modification engine 102, wearable devices 104a-b worn by users 106a-b, a trained machine-learning model 108, and client devices 112a-b. The components of the computing environment 100 may be communicatively coupled via a network 110, such as a local area network (LAN), wide area network (WAN), the Internet, or any combination thereof.

Examples of the wearable devices 104a-b can include smart watches, smart glasses, activity trackers, or any other electronic device worn on the skin. The wearable devices 104a-b may detect biological sets of biological data 114a-b with respect to the users 106a-b. For example, the first wearable device 104a may be a fitness tracker that can detect heart rate, calories burned, steps walked, and blood pressure of the first user 106a. The wearable devices 104a-b may transmit the sets of biological data 114a-b measured for the users 106a-b to the modification engine 102 via the network 110.

Examples of the client devices 112a-b can include a desktop computer, laptop computer, server, mobile phone, wearable device, or tablet. The client devices 112a-b may be associated with the users 106a-b that can interact with user interface 116 or video conference user interface (UI) 126 through the client devices 112a-b. The user interface 116 may be associated with a digital messaging application such as email or text messaging. The user interface 116 can include a first avatar 118a associated with the first user 106a. For example, the first avatar 118a may be depicted in emails or messages sent by the first user 106a on the first client device 112a. The first avatar 118a may be a digital representation of the first user 106a, such as a cartoon representation or a camera picture of the first user 106a. Similarly, the video conference UI 126 can include a second avatar 118b associated with the second user 106b. The second avatar 118b can be used to represent the second user 106b in a video conference UI 126 displayed on the second client device 112b. The first user 106 can also participate in the video conference, represented as the first avatar 118a.

To better communicate the emotional state of the users 106a-b when communicating via the user interface 116 or the video conference UI 126, the avatars 118a-b can be modified based on the sets of biological data 114a-b. The modification engine 102 can make adjustments to the user interface 116 or the video conference UI 126. For example, the modification engine 102 can receive the first set of biological data 114a for the first user 106a from the first wearable device 104a. The modification engine 102 can input the first set of biological data 114a into a trained machine-learning model 108. The trained machine-learning model 108 can be an algorithm that is trained using historical data 136 to make predictions or decisions. For example, the trained machine-learning model 108 may detect patterns within the historical data 136 and these patterns may be used to make predictions or decisions in relation to new data, such as the first set of biological data 114a. The trained machine-learning model 108 can be generated by training a machine-learning model using historical data 136 that includes historical emotional states 138 associated with historical biological data 140, as well as historical images 142 depicting the historical emotional states 138.

The trained machine-learning model 108 can generate a modified avatar 122 for the first avatar 118a based on the input. For example, the trained machine-learning model 108 can determine an emotional state 120 of the first user 106a based on the first set of biological data 114a. In a particular example, the trained machine-learning model 108 can determine that the first user 106a is in an emotional state of high stress. This may be due to patterns detected in the first set of biological data 114a, such as elevated heart rate or blood pressure. The trained machine-learning model 108 can also modify the first avatar 118a to display the emotional state 120 of the first user 106a. This modified avatar 122 may display a facial expression demonstrating high-stress emotions. The trained machine-learning model 108 can output the modified avatar 122 to the modification engine 102.

After receiving the modified avatar 122, the modification engine 102 can incorporate the modified avatar 122 into the user interface 116. For example, the modification engine 102 can replace the first avatar 118a with the modified avatar 122 for messages sent via the user interface 116 for a predetermined amount of time after the first set of biological data 114a is detected by the first wearable device 104a. The modification engine 102 can then output the user interface 116 with the modified avatar 122 for display to the first client device 112a, or to any other client device displaying the user interface 116. This can indicate to a receiver of the message, such as the second user 106b, that the message was sent when the first user 106a was in a stressed emotional state. Indicating that the first user 106a was in the stressed emotional state may provide further context to contents of the message, which may have otherwise been misinterpreted by the second user 106b.

It is common for users participating in video conference calls to turn off the video element and participate using only voice. As facial cues for such users are not available, it may be difficult for other users in the video conference call to determine reactions of users not participating via video, especially if such users mute their voice element as well. In such examples, the avatars 118a-b displayed on the video conference UI 126 can be similarly adjusted by the modification engine 102 to display modified avatars 122 generated by the trained machine-learning model 108. Additionally, the trained machine-learning model 108 can be used to generate a composite avatar 130 for users 106a-b in a video conference call. The composite avatar 130 can display an emotional state that represents the general feelings of users 106a-b on the video conference call. In some examples, the composite avatar 130 can be displayed on the video conference UI 126 in place of modified avatars 122 for individual users 106. This can provide participants in the video conference call with audience feedback while protecting the privacy of the emotional states for individual users.

To generate the composite avatar 130, the modification engine 102 may receive a second set of biological data 114b for the second user 106b from the second wearable device 104b. The modification engine 102 may provide the first set of biological data 114a, the first avatar 118a associated with the first user 106a, the second set of biological data 114b, and the second avatar 118b associated with the second user 106b as input to the trained machine-learning model 108. For example, the trained machine-learning model 108 can determine a composite emotional state 128 of the users 106a-b in the video conference call based on the input. The trained machine-learning model 108 can then generate a composite avatar 130 based on the avatars 118a-b. The composite avatar 130 can display the composite emotional state 128. The modification engine 102 can receive the composite avatar 130 from the trained machine-learning model 108 and can modify the video conference UI 126 to include the composite avatar 130.

In some examples, the trained machine-learning model 108 can be used to generate indications of emotional states beyond modification of avatars. For example, in response to receiving the first set of biological data 114a as input from the modification engine 102, the trained machine-learning model 108 can generate a color indicator 124 based on the emotional state 120 of the first user 106a. The color indicator 124 can include one or more colors to display the emotional state 120. For example, the color indicator 124 may be red to indicate that the first user 106a is experiencing negative emotions such as anger or stress, or green to indicate that the first user 106a is happy. In other examples, the color indicator 124 may include multiple colors to depict multiple emotions that the first user 106a may be experiencing based on the first set of biological data 114a. For example, the first set of biological data 114a can indicate that the first user 106a is primarily happy but slightly stressed. The trained machine-learning model 108 can generate a color indicator 124 that is a pie chart. The color indicator 124 may include 80% green and 20% red to reflect the emotional state. In some examples, the trained machine-learning model 108 may generate any other type of indicator, such as a symbol, to represent the emotional state 120. The trained machine-learning model 108 may similarly generate color indicators 124 for multiple users 106*a-b*, such as multiple users 106*a-b* participating in a video conference call via the video conference UI 126.

The modification engine 102 can receive the color indicator 124 or any other indicators from the trained machine-learning model 108. In some examples, the modification engine 102 can incorporate the color indicator 124 into the user interface 116 or the video conference UI 126 near the modified avatar 122 or composite avatar 130. In other examples, the color indicator 124 can be a color filter added on top of to the modified avatar 122 or the composite avatar 130.

In some examples, the modification engine 102 can use the color indicator 124 to determine suggested modifications 134 to digital communications 132 sent by a user. For example, the user interface 116 may be a digital communication user interface, such as an email user interface. The user may interact with the user interface 116 to compose a digital communication 132, such as an email, to be transmitted from the first client device 112*a* to the second client device 112*b*. Before the digital communication 132 is transmitted, the modification engine 102 can analyze the contents of the digital communication 132. If the color indicator 124 is indicating certain emotional states, such as anger or frustration, the modification engine 102 may determine a suggested modification 134 to the digital communication 132. For example, the modification engine 102 may generate a suggested modification 134 that re-words the digital communication 132 to include more neutral and less emotionally charged language. The modification engine 102 can output the suggested modification 134 for display on the user interface 116. If the first user 106*a* selects the suggested modification 134, the modification engine 102 can implement the suggested modification 134 to the digital communication 132 before transmitting the digital communication 132 to the second client device 112*b*.

Although FIG. 1 depicts a certain number and arrangement of components, this is for illustrative purposes and intended to be non-limiting. Other examples may include more components, fewer components, different components, or a different arrangement of the components shown in FIG. 1.

Figure 2:
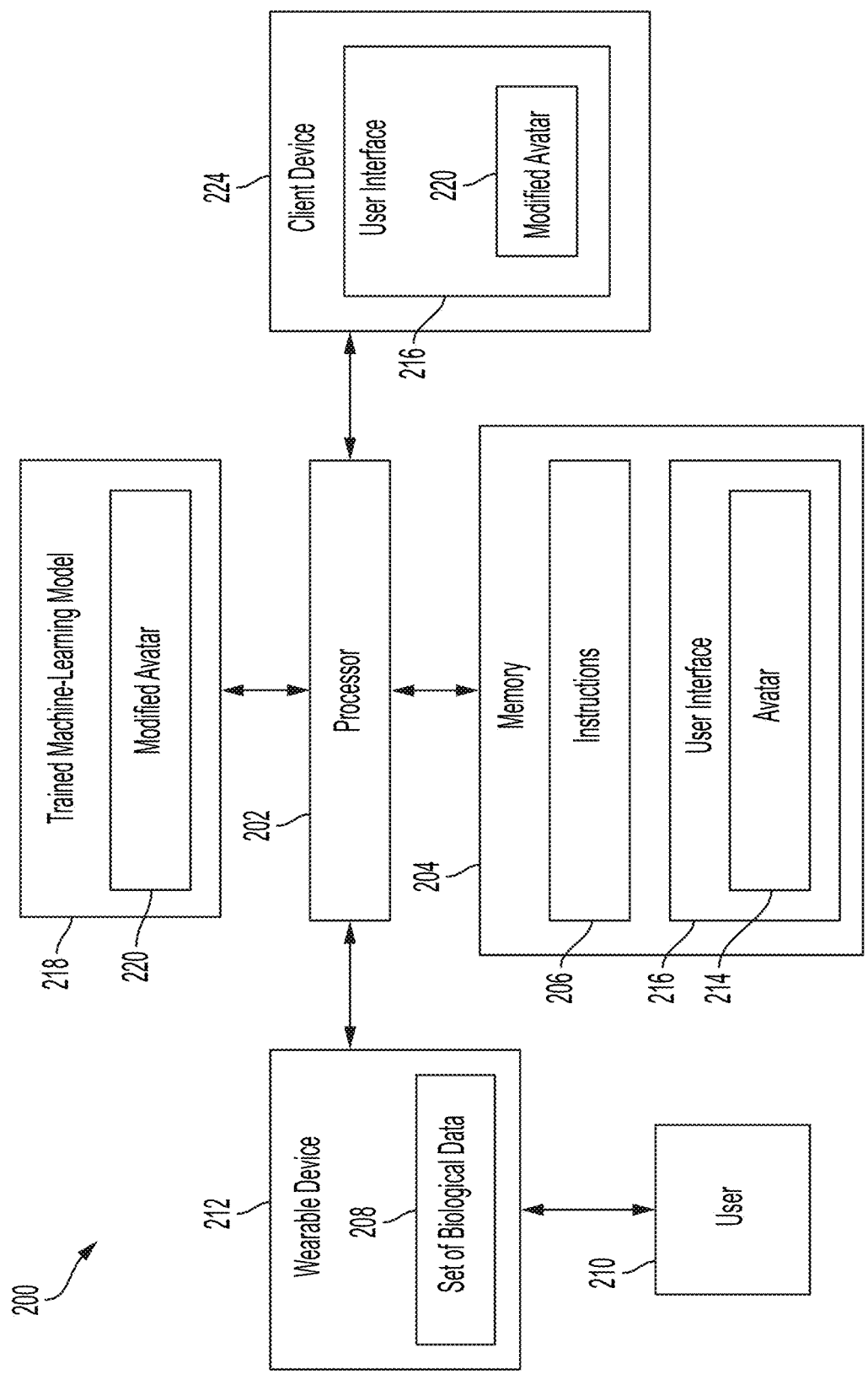
FIG. 2 is a block diagram of another example of a computing environment for using machine learning to modify an avatar on a user interface according to some examples of the present disclosure.

FIG. 2 is a block diagram of another example of a computing environment 200 for using machine learning to modify an avatar 214 on a user interface 216 according to some examples of the present disclosure. The computing environment 200 includes a processor 202 communicatively coupled to a memory 204. These components may be internal to a housing of the computing device environment or can be distributed and remote from one another. The processor 202 can also be communicatively coupled to a wearable device 212, a client device 224, and a trained machine-learning model 218. The client device 224 may include a user input device for a user, such as a user 210 wearing the wearable device 212, to interact with a user interface 216 on the client device 224. Examples of such user input devices can include a keyboard, mouse, or touch-screen display. The client device 224 can include one display device or multiple display devices. Examples of such display devices can include a liquid crystal display (LCD) and a light-emitting diode (LED) display.

The processor 202 can include one processor or multiple processors. Non-limiting examples of the processor 202 include a Field-Programmable Gate Array (FPGA), an application-specific integrated circuit (ASIC), or a microprocessor. The processor 202 can execute instructions 206 stored in the memory 204 to perform operations. In some examples, the instructions 206 can include processor-specific instructions generated by a compiler or an interpreter from code written in any suitable computer-programming language, such as C, C++, C#, etc.

The memory 204 can include one memory or multiple memories. The memory 204 can be non-volatile and may include any type of memory that retains stored information when powered off. Non-limiting examples of the memory 204 include electrically erasable and programmable read-only memory (EEPROM), flash memory, or any other type of non-volatile memory. At least some of the memory can include a non-transitory computer-readable medium from which the processor 202 can read instructions 206. A computer-readable medium can include electronic, optical, magnetic, or other storage devices capable of providing the processor 202 with computer-readable instructions or other program code. Examples of the non-transitory computer-readable medium include magnetic disk(s), memory chip(s), ROM, random-access memory (RAM), an ASIC, a configured processor, optical storage, or any other medium from which a computer processor can read the instructions 206.

The instructions 206 can be executed by the processor 202 to generate a modified user interface based on data from the wearable device 212. For example, the processor 202 can receive a set of biological data 208 for the user 210 from the wearable device 212 worn by the user 210. The user 210 can be associated with an avatar 214 of the user 210 on the user interface 216. The processor 202 can provide the avatar 214 and the set of biological data 208 as input to a trained machine-learning model 218. The trained machine-learning model 218 can generate a modified avatar 220 based on the input. The processor 202 can then receive the modified avatar 220 as output from the trained machine-learning model 218. The processor 202 can modify the user interface 216 to include the modified avatar 220 and can output the modified user interface 216 for display on the client device 224.

Figure 3:
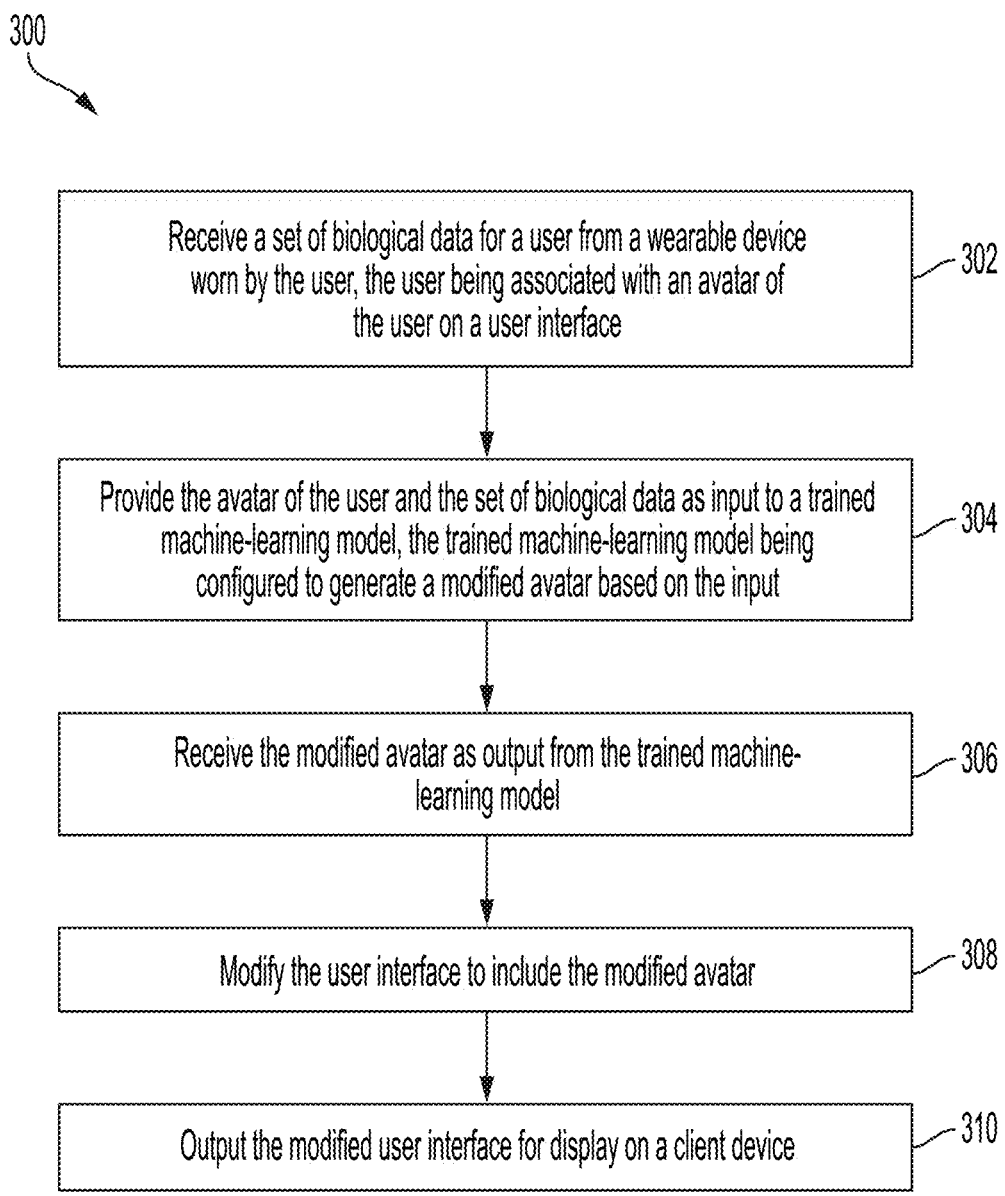
FIG. 3 is a flowchart of a process for using machine learning to adjust an avatar on a user interface according to some examples of the present disclosure.

In some examples, the processor 202 can implement some or all of the steps shown in FIG. 3. Other examples may involve more steps, fewer steps, different steps, or a different order of the steps than is shown in FIG. 3. The steps of FIG. 3 are described below with reference to components described above in regard to FIGS. 1-2.

Turning now to FIG. 3, the process 300 begins at block 302 with receiving, by the processor 202, a set of biological data 208 for a user 210 from a wearable device 212 worn by the user 210, the user 210 being associated with an avatar 214 of the user 210 on a user interface 216. For example, the wearable device 212 may be a fitness tracker worn on the wrist of the user 210. The fitness tracker can measure the set of biological data 208 for the user 210, which may include hours of sleep, heart rate, and blood pressure for the user 210. The wearable device 212 can transmit the set of biological data 208 to the processor 202. In some examples, the wearable device 212 can transmit the set of biological data 208 to the processor 202 at periodic intervals, such as once per day or once per hour. Additionally or alternatively, the wearable device 212 can transmit the set of biological data 208 to the processor 202 in response to an event. For example, the processor 202 may request the set of biological data 208 from the wearable device 212 in response to the user 210 interacting with the user interface 216 to send a digital communication such as an email.

At block 304, the process 300 involves providing, by the processor 202, the avatar 214 of the user 210 and the set of biological data 208 as input to a trained machine-learning model 218, the trained machine-learning model 218 being configured to generate a modified avatar 220 based on the input. The avatar 214 of the user 210 can be a headshot image of the user 210 depicted in the user interface 216. At block 306, the process 300 involves receiving, by the processor 202, the modified avatar 220 as output from the trained machine-learning model 218. The modified avatar 220 can be generated by the trained machine-learning model 218 to reflect an emotional state of the user 210 based on the set of biological data 208. For example, if the set of biological data 208 indicates that the user 210 is sleep deprived and tense, the modified avatar 220 may be a recreation of the avatar 214 showing such emotions. In the modified avatar 220, the face of the user 210 in the avatar 214 may be adjusted to yawn or frown to depict the emotional state.

At block 308, the process 300 involves modifying, by the processor 202, the user interface 216 to include the modified avatar 220. For example, the processor 202 can replace the avatar 214 with the modified avatar 220 in the user interface 216. In some examples, the processor 202 can replace all instances of the avatar 214 with the modified avatar 220 in the user interface 216. In other examples, the processor 202 can replace the avatar 214 with the modified avatar 220 in messages (such as text messages or emails) sent by the user 210 after the set of biological data 208 was transmitted by the wearable device 212.

Figure 4:
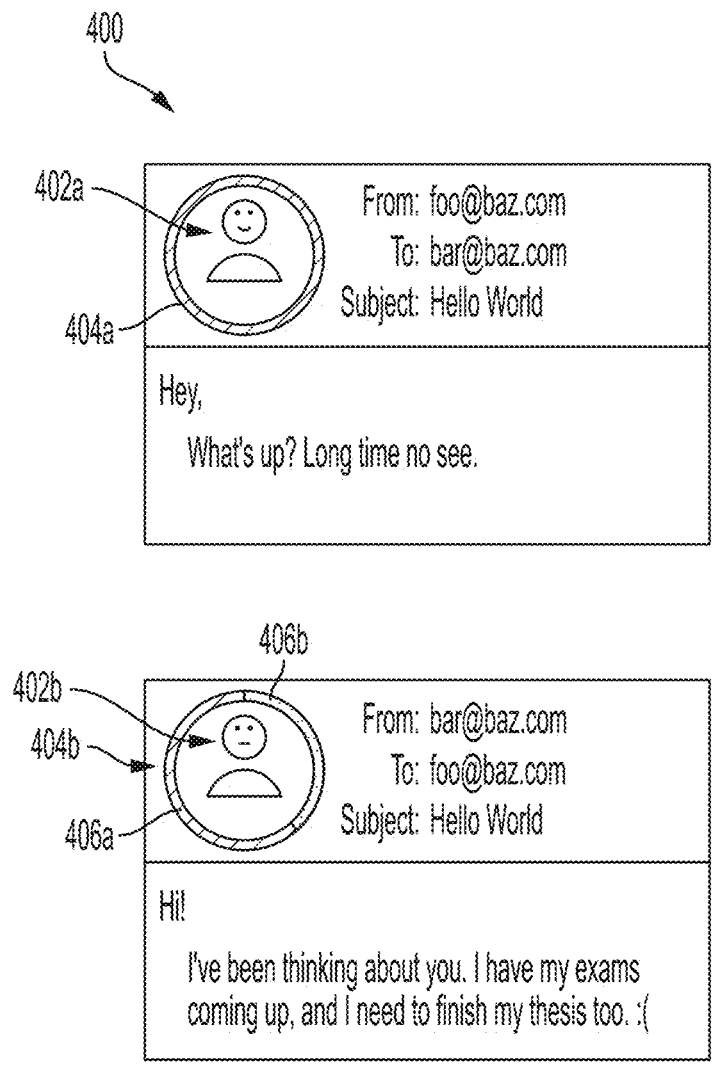
FIG. 4 is an example of a user interface modified based on biological data according to some examples of the present disclosure.

At block 310, the process 300 involves outputting, by the processor 202, the modified user interface 216 for display on a client device 224. One example of the modified user interface 216 including the modified avatar 220 is depicted in FIG. 4, which includes an email user interface 400. The email user interface 400 depicts a first email sent by a first user, represented with the first avatar 402a. Additionally, the email user interface 400 depicts a second email sent as a response to the first email by a second user, represented with the second avatar 402b. The first avatar 402a and second avatar 402b have each been modified by a trained machine-learning model to display emotional states of the users, based on biological data collected by wearable devices. The processor 202 modified the email user interface 400 to replace the original avatars with the first avatar 402a and the second avatar 404b. Additionally, the processor 202 received color indicators 404a-b for the users. The processor 202 modified the email user interface 400 to include the color indicators 404a-b around the modified avatars 402a-b.

The modified avatars 402a-b and the color indicators 404a-b can provide the users with additional context for the emails. For example, the first avatar 402a displays a smiling face, and the color indicator 404a depicts a single color that can represent a happy or positive mood, such as green. This can indicate to the second user that the first email was sent when the first user was in a positive mood. The second avatar 404b depicts a face that is neither smiling nor frowning, and the color indicator 406b depicts two colors. The first color 406a can be a color that represents a happy or positive mood, such as green. The second color 406b can be a color that represents a frustrated or negative mood, such as red. This can indicate to the first user that the second email was sent when the second user was in a mostly happy yet slightly stressed mood.

Figure 5:
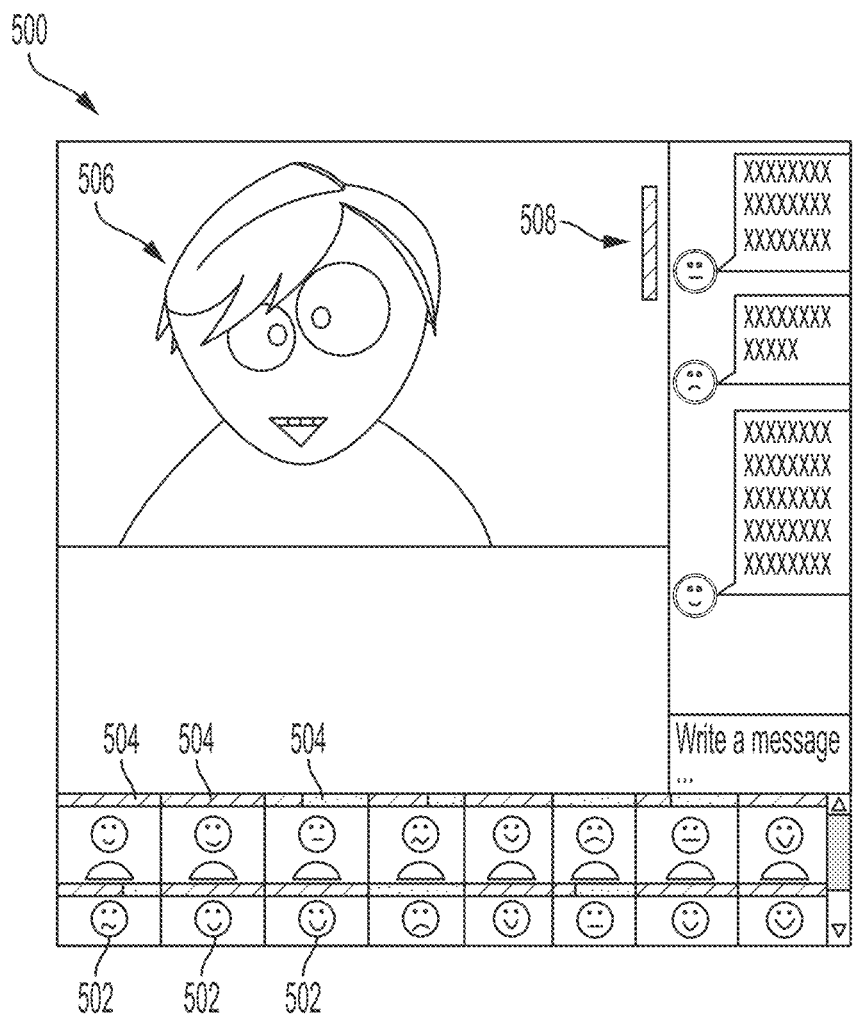
FIG. 5 is another example of a user interface modified based on biological data according to some examples of the present disclosure.

Another example of the modified user interface 216 is depicted in FIG. 5, which includes a video conference user interface (UI) 500. The video conference UI 500 can include multiple modified avatars 502 that have been generated by a trained machine-learning model based on biological data from wearable devices. Additionally, each of the modified avatars 502 is paired with a color indicator 504 including one or more colors to reflect an emotional state of the users. The video conference UI 500 can also include a composite avatar 506 and a composite color indicator 508 that reflects a composite emotional state of all users interacting with the video conference UI 500.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
a processor; and
a memory including instructions that are executable by the processor for causing the processor to:
receive a set of biological data for a user from a wearable device worn by the user, the user being associated with an avatar of the user on a user interface;
provide the avatar of the user and the set of biological data as input to a trained machine-learning model, the trained machine-learning model being configured to generate a modified avatar based on the input by:
determining an emotional state of the user based on the set of biological data;
determining a color indicator that indicates the emotional state of the user based on the set of biological data; and
modifying the avatar to display the emotional state of the user;
receive the modified avatar and the color indicator as output from the trained machine-learning model;
modify the user interface to include the modified avatar and the color indicator; and
output the modified user interface for display on a client device.

2. The system of claim 1, wherein the user interface is a digital communication user interface, and wherein the memory further comprises instructions that are executable by the processor for causing the processor to:
receive, from the user interacting with the digital communication user interface on the client device, a digital communication to be transmitted to another client device;
determine, based on the digital communication and the color indicator, a suggested modification to the digital communication; and
output the suggested modification for display on the digital communication user interface.

3. The system of claim 1, wherein the set of biological data is a first set of biological data with respect to a first user wearing a first wearable device, wherein the avatar is a first avatar on a first user interface, and wherein the memory further comprises instructions that are executable by the processor for causing the processor to:
receive a second set of biological data for a second user from a second wearable device worn by the user, the second user being associated with a second avatar on a second user interface;
provide the first set of biological data, the first avatar, the second set of biological data, and the second avatar as input to the trained machine-learning model, the trained machine-learning model being configured to generate a composite avatar based on the input;
receive the composite avatar as output from the trained machine-learning model; and
modify the user interface to include the composite avatar.

4. The system of claim 3, wherein the modified user interface is a video conference user interface, and wherein the composite avatar indicates a composite emotional state of the first user and the second user.

5. The system of claim 1, wherein the memory further comprises instructions that are executable by the processor for causing the processor to:
generate the trained machine-learning model by training a machine-learning model using historical data, the historical data indicating emotional states of historical sets of biological data.

6. A method comprising:
receiving, by a processor, a set of biological data for a user from a wearable device worn by the user, the user being associated with an avatar of the user on a user interface;
providing, by the processor, the avatar of the user and the set of biological data as input to a trained machine-learning model, the trained machine-learning model being configured to generate a modified avatar based on the input by:
determining an emotional state of the user based on the set of biological data;
determining a color indicator that indicates the emotional state of the user based on the set of biological data; and
modifying the avatar to display the emotional state of the user;
receiving, by the processor, the modified avatar and the color indicator as output from the trained machine-learning model;
modifying, by the processor, the user interface to include the modified avatar and the color indicator; and
outputting, by the processor, the modified user interface for display on a client device.

7. The method of claim 6, wherein the user interface is a digital communication user interface, and wherein the method further comprises:
receiving, from the user interacting with the digital communication user interface on the client device, a digital communication to be transmitted to another client device;
determining, based on the digital communication and the color indicator, a suggested modification to the digital communication; and
outputting the suggested modification for display on the digital communication user interface.

8. The method of claim 6, wherein the set of biological data is a first set of biological data for a first user wearing a first wearable device, wherein the avatar is a first avatar on a first user interface, and wherein the method further comprises:
receiving a second set of biological data for a second user from a second wearable device worn by the user, the second user being associated with a second avatar on a second user interface;
providing the first set of biological data, the first avatar, the second set of biological data, and the second avatar as input to the trained machine-learning model, the trained machine-learning model being configured to generate a composite avatar based on the input;
receiving the composite avatar as output from the trained machine-learning model; and
modifying the user interface to include the composite avatar.

9. The method of claim 8, wherein the modified user interface is a video conference user interface, and wherein the composite avatar indicates a composite emotional state of the first user and the second user.

10. The method of claim 6, further comprising:
generating the trained machine-learning model by training a machine-learning model using historical data, the historical data indicating emotional states of historical sets of biological data.

11. A non-transitory computer-readable medium comprising program code that is executable by a processor for causing the processor to:
receive a set of biological data for a user from a wearable device worn by the user, the user being associated with an avatar of the user on a user interface;
provide the avatar of the user and the set of biological data as input to a trained machine-learning model, the trained machine-learning model being configured to generate a modified avatar based on the input by:
determining an emotional state of the user based on the set of biological data;
determining a color indicator that indicates the emotional state of the user based on the set of biological data; and
modifying the avatar to display the emotional state of the user;
receive the modified avatar and the color indicator as output from the trained machine-learning model;
modify the user interface to include the modified avatar and the color indicator; and
output the modified user interface for display on a client device.

12. The non-transitory computer-readable medium of claim 11, wherein the user interface is a digital communication user interface, and wherein the program code is further executable by the processor for causing the processor to:
receive, from the user interacting with the digital communication user interface on the client device, a digital communication to be transmitted to another client device;
determine, based on the digital communication and the color indicator, a suggested modification to the digital communication; and
output the suggested modification for display on the digital communication user interface.

13. The non-transitory computer-readable medium of claim 11, wherein the set of biological data is a first set of biological data with respect to a first user wearing a first wearable device, wherein the avatar is a first avatar on a first user interface, and wherein the program code is further executable by the processor for causing the processor to:
receive a second set of biological data for a second user from a second wearable device worn by the user, the second user being associated with a second avatar on a second user interface;
provide the first set of biological data, the first avatar, the second set of biological data, and the second avatar as input to the trained machine-learning model, the trained machine-learning model being configured to generate a composite avatar based on the input;
receive the composite avatar as output from the trained machine-learning model; and
modify the user interface to include the composite avatar.

14. The non-transitory computer-readable medium of claim 13, wherein the modified user interface is a video conference user interface, and wherein the composite avatar indicates a composite emotional state of the first user and the second user.

\* \* \* \* \*